United States Patent [19]

Grams et al.

[11] 4,052,980

[45] Oct. 11, 1977

[54] TRIAXIAL FIBEROPTIC SOFT TISSUE RETRACTOR

[75] Inventors: Guenter A. Grams, Costa Mesa; Frederick M. Grazer, Newport Beach, both of Calif.

[73] Assignee: Guenter A. Grams, Costa Mesa, Calif.

[21] Appl. No.: 694,895

[22] Filed: June 10, 1976

[51] Int. Cl.² ............................................. A61B 1/06
[52] U.S. Cl. ...................................... 128/18; 128/20
[58] Field of Search ................... 128/17, 18, 20, 12

[56] References Cited

U.S. PATENT DOCUMENTS

| | | | |
|---|---|---|---|
| 786,457 | 4/1905 | McGinnis | 128/17 |
| 2,809,628 | 10/1957 | Jonas | 128/17 |
| 3,616,792 | 11/1971 | Pleet | 128/11 |

FOREIGN PATENT DOCUMENTS

| | | | |
|---|---|---|---|
| 549,791 | 12/1942 | United Kingdom | 128/18 |

*Primary Examiner*—Robert W. Michell
*Assistant Examiner*—Henry S. Layton
*Attorney, Agent, or Firm*—Lyon & Lyon

[57] ABSTRACT

A surgical retractor instrument having a first pair of fingers of small diameter fixed to one end of a handle and extending therefrom in essentially parallel relation in a lateral direction, the fingers being joined at their extremities to form an open loop. A second pair of fingers, also of small diameter, pivotally secured to the handle near the first pair of fingers and extending in the same general direction as the first pair of fingers, the extremities of the second pair of fingers terminating in closed loops, the loops of the second pair of fingers being movable between a retracted contiguous position within the open loop joining the first pair of fingers and an extended position forming with the open loop the apeces of a triangle. The second pair of fingers being spring biased to the contiguous position and movable by a lever extending along the handle. The lever being manually engageable to spread the closed loops toward their extended position, and engage a latch pin extending from the handle to maintain the closed loops in their extended position. The surgical instrument, when the open loops are in contiguous relation is insertable into a small entrance incision formed in a patient, and after insertion is expandable to retract the walls of the surrounding cavity in the patient and enlarge the cavity for surgical operation. The instrument including a fiberoptic light for illuminating the cavity.

10 Claims, 8 Drawing Figures

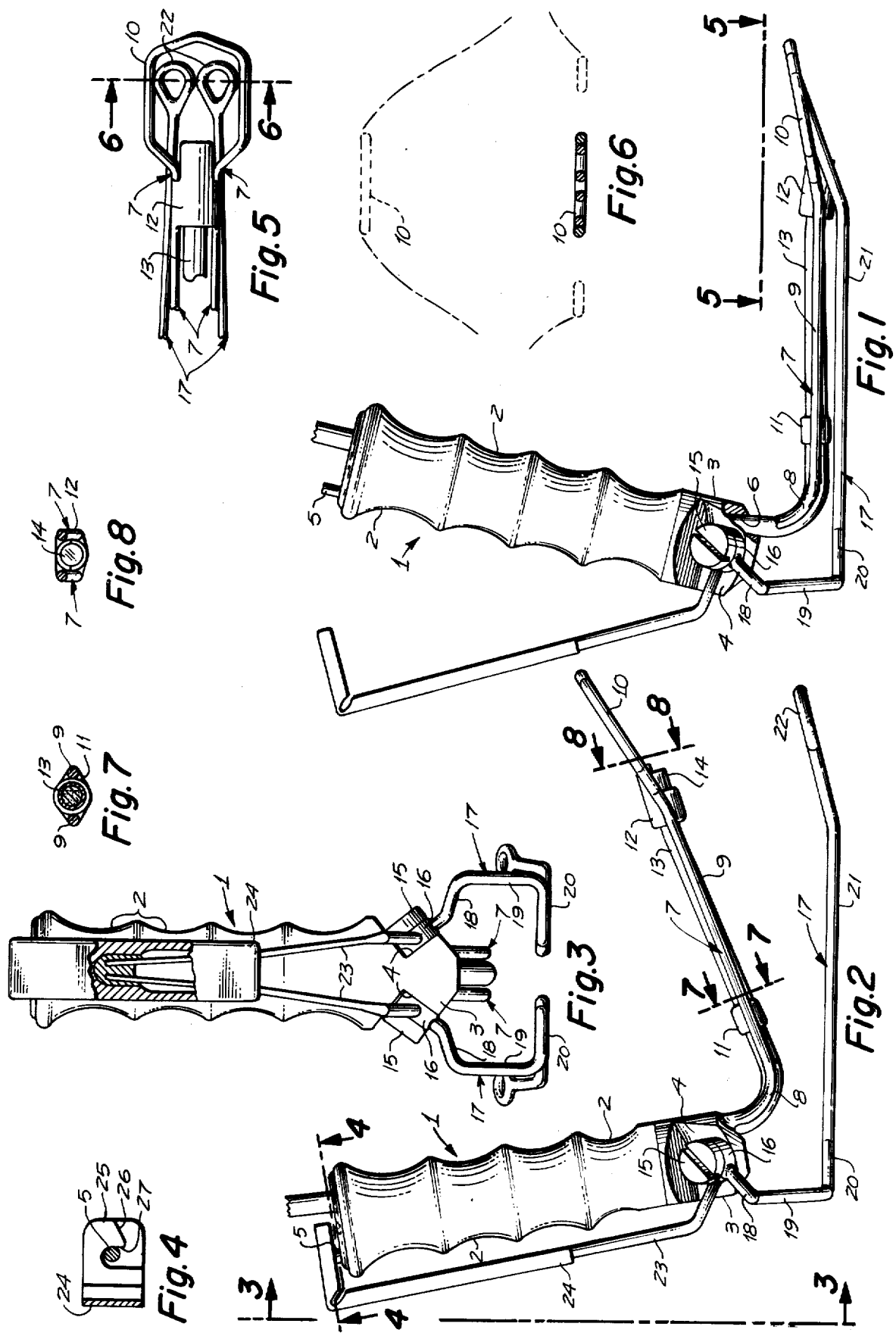

TRIAXIAL FIBEROPTIC SOFT TISSUE RETRACTOR

BACKGROUND

A commonly encountered surgical situation involves the forming of a small incision, then inserting a blade speculum or retractor to spread the incision. Often several such instruments are needed and must be hand held by the surgeon's assistants in order that the surgeon may perform the operation.

SUMMARY

The present invention is directed to a triaxial fiberoptic soft tissue retractor which greatly simplifies the maintanence of an appropriate cavity during surgery and is summarized in the following objects:

First, to provide a soft tissue retractor which may be readily manipulated by one hand and thus permitting the surgeon to utilize the retractor while also performing such surgery or other treatment as required with the other hand.

Second, to provide a retractor as indicated in the previous object, in which novelly arranged further elements of small diameter form the apeces of a triangular cavity forming structure with minimal obstruction at the entrance incision so as to permit maximum view of the cavity, as well as maximum exposure of and access to the surface of the cavity.

Third, to provide an instrument as indicated in the other objects, which is so arranged as to receive a sleeve encased fiberoptic handle to provide adequate illumination of the cavity.

Fourth, to provide in an instrument as indicated in the other objects which includes an easily manipulatable latch means so arranged that the instrument may be locked in its open position permitting the instrument to be self supporting so as to free both hands of the surgeon for performing surgery.

Fifth, to provide triaxial fiberoptic soft tissue retractor which materially increases the size of the cavity which may be formed in a patient while minimizing the size of the entrance incision so that the resulting surface scar is minimal, and which materially reduces the number of assistants needed in the surgery zone.

DESCRIPTION OF THE FIGURES

FIG. 1 is a side view of the triaxial fiberoptic soft tissue retractor, shown in its retracted position.

FIG. 2 is a similar side view showing the retractor in its extended position.

FIG. 3 is an end view taken from 3—3 of FIG. 2.

FIG. 4 is a transverse sectional view taken through 4—4 of FIG. 2, illustrating the latch means.

FIG. 5 is a fragmentary top view taken from 5—5 of FIG. 1.

FIG. 6 is a sectional view taken from 6—6 of FIG. 5, showing by solid lines the fingers of the retractor in their contiguous position and by broken lines in their extended position.

FIG. 7 and 8 are transverse sectional views taken through 7—7 and 8—8 of FIG. 2.

DETAILED DESCRIPTION

The triaxial fiberoptic soft tissue retractor includes a handle 1 which is tubular, and provided with finger receiving recesses 2, the lower end 3 of the handle is closed and provided with journal recesses 4 which converge downwardly. Extending upwardly from the upper end of the handle is a latch pin 5 and the closed lower end 3 is provided with a passageway 6 to receive a fiberoptic bundle, to be described hereinafter.

Secured to the lower end of the handle 1 at opposite sides of the passageway 6 is a pair of fixed fingers 7 which include downwardly and laterally curved portions 8 joined to an essentially coplanar straight portions 9, which are joined at their extremities to an upwardly tilted open loop 10, the lateral dimension of the open loop is greater than the spacing between the straight portions 9.

Connecting the portions 9 near the handle 1, is a fiberoptic bundle retainer 11 and at the juncture between the portions 9 and the loop 10 is a fiberoptic bundle end retainer 12.

Extending through the passageway 6 and secured between the fingers 7, by the retainers 11 and 12, is a fiberoptic bundle 13 which may be conventional, the fiberoptic bundle includes a plurality of optical fibers encased in a flexible sleeve. The fiberoptic bundle terminates in a light emitting end 14 secured in the retainer 12.

Retained in the journal recesses 4 by journal screws 15, is a pair of pivot disks 16, secured to the pivot disks is a pair of movable fingers 17 including diverging portions 18 laterally spaced parallel portions 19 and abruptly converging portions 20 which are joined to slightly converging straight portions 21, which terminate in loop tips 22. The length of the fixed fingers 7 and movable fingers 17 are approximately the same and their extremities tip upward slightly. The dimensions of the guide loop 10 and loop tips 22 are such that the loop tips fit within the guide loop, as shown in FIGS. 1, 5 and 6.

Secured to the pivot disks 16 is a pair of spring lever arms 23 which extend upwardly along side the handle 1 and are encased in a lever strip 24 terminating at its upper end in a lateral latch plate 25, capable of overlapping the upper end of the handle 1. The under side of the latch plate 25 which confronts the end of the handle 1 is provided with a latch cam 26 and a latch recess 27 engaged by the latch pin 5.

Operation of the triaxial fiberoptic soft tissue retractor is as follows:

The biasing effect of the spring arms 23 is such that the movable fingers 17 are urged into contiguous relation with each other and the fixed fingers 7, as shown in FIGS. 1 and 5. In this position the spring arms and lever strip diverge upwardly from the handle 1, and the fingers 7 and 17 are in contiguous relation and the tips 22 are within the open loop 10. With the fingers in contiguous relation their extended ends are readily inserted into an incision of relatively small dimension. Once the guide loop 10 has entered a cavity acessible through the incision the spacing of the fingers permit the insertion to be continued until the secured ends of the fingers are in proximity to the incision. After the fingers have been so inserted, the lever strip 24 is moved toward the handle, that is, toward the position shown in FIG. 2. This movement of the lever causes the movable fingers 17 to move downward with respect to the fixed fingers and at the same time move in divergent directions with respect to each other, as well as the open loop 10; that is , the extended portions of the fixed and movable fingers move from the solid line position shown in FIG. 6 to the dotted line position shown therein. This is accomplished with minimal stretching of the initial incision.

As the walls of the cavity become fully retracted the latch plate 25 moves over the pin 5 and the pin is guided by the latch cam 26 into the latch recess 27 so that the fingers are retained in the position shown in FIG. 2. When it is desired to release the fingers, it is merely necessary to push laterally with one's thumb against the lever strip 24 causing the pin 5 to clear the latch recess 27. By reason of the lateral extension adjacent to the attached portions of the movable fingers 17, the view into the cavity is limited only by the dimensions of the initial incision, as is apparent from FIG. 3.

Having fully described our invention it is to be understood that we are not to be limited to the details herein set forth, but that our invention is of the full scope of the appended claims.

We claim:

1. A surgical instrument for insertion through an incision of minimal dimension into a cavity therebeyond, said instrument comprising:
   a. a handle means;
   b. a set of fingers extending therefrom and normally disposed in contiguous relation for insertion through the incision into the cavity;
   c. means for causing the fingers to diverge with minimal divergence in the region of the incision and maximum divergence at the extremities of the fingers within the cavity thereby to effect retraction of the cavity walls;
   d. the set of fingers including a relatively fixed pair of fingers joined at their extremities and a second pair of fingers;
   e. the diverging means including a pair of pivot members movable about converging axes, and the second pair of fingers are secured thereto for diverging movement from the fixed fingers and from each other;
   f. the diverging means further including a lever member extending alongside the handle means for manual gripping engagement and connected to the pivot members to effect movement thereof.

2. A surgical instrument as defined in claim 1, wherein:
   a. a fiberoptic bundle having a light emitting end which extends from the handle and is carried by selected fingers to place its light emitting end in position for illuminating the cavity.

3. A surgical instrument as defined in claim 1, wherein:
   a. the diverging means further includes, yieldable means biasing the lever member to cause convergence of the fingers, and cooperating latch means on the handle and lever are interengageable to retain the fingers in their divergent position.

4. A surgical instrument adapted to be inserted through a small incision and expanded to retract soft tissue to form a cavity for surgical access, said instrument comprising:
   a. a handle member contoured to be gripped by the user's hand;
   b. a pair of fixed finger elements secured to and extending laterally from one end of the handle member, the finger elements being joined at their extremities to form an open loop;
   c. a pair of pivot means secured to the handle member adjacent said end and defining convergent pivotal axes;
   d. a pair of movable finger elements secured to the pivot means and movable thereby between positions contiguous each other and to the pair of fixed finger elements and positions divergent from each other and the fixed finger elements;
   e. and a lever member connected to the pivot means to effect movement of the movable finger elements upon movement of the extremity of the lever member to and from the handle member, the lever member being biased away from the handle member to urge the movable finger elements toward their contiguous position.

5. A surgical instrument as defined in claim 4, which further comprises:
   a. manually operable elements carried by the handle member and lever member for releasable interengagement to retain the movable finger element in their divergent position.

6. A surgical instrument as defined in claim 4, which further comprises:
   a. a fiberoptic bundle having a light emitting extremity extending through the handle and between the fixed finger elements.

7. A surgical instrument adapted to be inserted through a small incision and expanded to retract soft tissue to form a cavity for surgical access, said instrument comprising:
   a. a handle member contoured to be gripped by the user's hand;
   b. a fixed finger means secured to and extending laterally from one end of the handle member;
   c. a pair of pivot means secured to the handle member adjacent said one end and defining convergent pivotal axes;
   d. a lever member connected to both pivot means and extending alongside the handle to be gripped therewith to effect pivotal movement of the pivot means about their convergent axes; and
   e. a pair of movable finger elements secured to the pivot means and movable thereby between positions contiguous to each other and the fixed finger means, and positions divergent from each other and the fixed finger means.

8. A surgical instrument, as defined in claim 7, wherein:
   a. said lever member includes spring arms producing a biasing force urging the finger elements toward their contiguous positions;
   b. and means for latching the lever member to the handle to retain the finger elements in their divergent positions.

9. A surgical instrument, as defined in claim 7, wherein:
   a. a fiberoptic bundle having a light emitting extremity extends longitudinally through the fixed finger means.

10. A surgical instrument, as defined in claim 7, wherein:
   a. the finger means includes a guide tip receiving the tips of the finger elements to facilitate insertion through the incision.

* * * * *